(12) United States Patent
Gross et al.

(10) Patent No.: US 11,160,459 B2
(45) Date of Patent: Nov. 2, 2021

(54) MONITORING HEALTH STATUS OF PEOPLE SUFFERING FROM CHRONIC DISEASES

(71) Applicant: ChroniSense Medical Ltd., Yokneam (IL)

(72) Inventors: Yossi Gross, Moshav Mazor (IL); Daniel H. Lange, Kfar Vradim (IL)

(73) Assignee: ChroniSense Medical Ltd., Yokneam (IL)

( * ) Notice: Subject to any disclaimer, the term of this patent is extended or adjusted under 35 U.S.C. 154(b) by 0 days.

(21) Appl. No.: 14/738,666

(22) Filed: Jun. 12, 2015

(65) Prior Publication Data
US 2016/0360971 A1   Dec. 15, 2016

(51) Int. Cl.
*A61B 5/0205*   (2006.01)
*A61B 5/00*   (2006.01)
(Continued)

(52) U.S. Cl.
CPC ........ *A61B 5/0205* (2013.01); *A61B 5/02416* (2013.01); *A61B 5/4082* (2013.01);
(Continued)

(58) Field of Classification Search
CPC ... A61B 5/0205; A61B 5/4082; A61B 5/4818; A61B 5/4833; A61B 5/6824;
(Continued)

(56) References Cited

U.S. PATENT DOCUMENTS 3,885,552 A   5/1975   Kennedy
3,898,984 A   8/1975   Mandel et al.
(Continued)

FOREIGN PATENT DOCUMENTS

CN   1335756 A   2/2002
CN   106901747 A   6/2017
(Continued)

OTHER PUBLICATIONS

Arza et al., "Pulse Transit Time and Pulse Width as Potential Measure for estimating Beat-to-Beat Systolic and Diastolic Blood Pressure", Computing in Cardiology 2013, pp. 887-890.
(Continued)

*Primary Examiner* — Lynsey C Eiseman
*Assistant Examiner* — Jessandra F Hough
(74) *Attorney, Agent, or Firm* — Carr & Ferrell LLP

(57) ABSTRACT

Methods and systems for monitoring health status of chronically ill people are provided. An example system includes a wearable device with sensors, with the wearable device being designed to be worn on a wrist of a patient. The wearable device is operable to continuously collect, via sensors, sensor data from a single place on body of the patient. The sensor data are processed to obtain electrocardiogram data and photoplethysmogram data. The electrocardiogram data and the photoplethysmogram data are analyzed to obtain medical parameters associated with a chronic disease. Based at least partially on the changes in the medical parameters over time, a progression of the at least one chronic disease can be determined. Based on the progression, messages regarding the current health condition are sent to the patient. The messages include advice to take medicine or contact a medical professional if a chronic condition is worsening.

20 Claims, 10 Drawing Sheets

(51) Int. Cl.
<table>
<tr><td>G16H 40/63</td><td>(2018.01)</td></tr>
<tr><td>A61B 5/024</td><td>(2006.01)</td></tr>
<tr><td>G16H 40/67</td><td>(2018.01)</td></tr>
<tr><td>A61B 5/349</td><td>(2021.01)</td></tr>
<tr><td>A61B 5/02</td><td>(2006.01)</td></tr>
<tr><td>A61B 5/021</td><td>(2006.01)</td></tr>
<tr><td>A61B 5/029</td><td>(2006.01)</td></tr>
<tr><td>A61B 5/08</td><td>(2006.01)</td></tr>
<tr><td>A61B 5/11</td><td>(2006.01)</td></tr>
<tr><td>A61B 5/1455</td><td>(2006.01)</td></tr>
</table>

(52) U.S. Cl.
CPC .......... *A61B 5/4818* (2013.01); *A61B 5/4833* (2013.01); *A61B 5/6824* (2013.01); *A61B 5/7275* (2013.01); *A61B 5/746* (2013.01); *G16H 40/63* (2018.01); *A61B 5/0022* (2013.01); *A61B 5/021* (2013.01); *A61B 5/02007* (2013.01); *A61B 5/029* (2013.01); *A61B 5/0816* (2013.01); *A61B 5/11* (2013.01); *A61B 5/14551* (2013.01); *A61B 5/349* (2021.01); *A61B 2562/046* (2013.01); *A61B 2562/06* (2013.01); *G16H 40/67* (2018.01)

(58) Field of Classification Search
CPC ..... A61B 5/746; A61B 5/02007; A61B 5/021; A61B 5/02416; A61B 5/029; A61B 5/0452; A61B 5/0816; A61B 5/11; A61B 5/14551; A61B 5/7275; A61B 5/0022; A61B 2562/046; A61B 2562/06; G06F 19/30; G16H 40/67; G16H 40/63
See application file for complete search history.

(56) References Cited

U.S. PATENT DOCUMENTS

| | | | |
|---|---|---|---|
| 4,331,154 A * | 5/1982 | Broadwater | A61B 5/021 |
| | | | 600/490 |
| 4,732,158 A | 3/1988 | Sadeh | |
| 4,802,486 A | 2/1989 | Goodman et al. | |
| 5,050,612 A | 9/1991 | Matsumura | |
| 5,316,008 A | 5/1994 | Suga et al. | |
| 5,503,148 A | 4/1996 | Pologe et al. | |
| 5,692,505 A | 12/1997 | Fouts | |
| 6,047,203 A | 4/2000 | Sackner et al. | |
| 6,139,494 A * | 10/2000 | Cairnes | G06F 19/345 |
| | | | 600/300 |
| 6,527,725 B1 | 3/2003 | Inukai et al. | |
| 7,184,809 B1 | 2/2007 | Sterling et al. | |
| 7,479,111 B2 | 1/2009 | Zhang et al. | |
| 7,544,168 B2 | 6/2009 | Nitzan | |
| 7,738,935 B1 | 6/2010 | Turcott | |
| 8,172,764 B2 | 5/2012 | Gregson et al. | |
| 8,602,997 B2 | 12/2013 | Banet et al. | |
| 8,866,606 B1 * | 10/2014 | Will | H04W 4/22 |
| | | | 340/539.11 |
| 10,470,692 B2 | 11/2019 | Lange et al. | |
| 10,687,742 B2 | 6/2020 | Lange et al. | |
| 10,952,638 B2 | 3/2021 | Lange | |
| 11,000,235 B2 | 5/2021 | Lange | |
| 2001/0005773 A1 | 6/2001 | Larsen et al. | |
| 2001/0029326 A1 | 10/2001 | Diab et al. | |
| 2002/0095077 A1 | 7/2002 | Swedlow et al. | |
| 2002/0133068 A1 | 9/2002 | Huiku | |
| 2003/0009091 A1 | 1/2003 | Edgar, Jr. et al. | |
| 2003/0036685 A1 * | 2/2003 | Goodman | A61B 5/0002 |
| | | | 600/300 |
| 2003/0065269 A1 * | 4/2003 | Vetter | A61B 5/02416 |
| | | | 600/503 |
| 2003/0109776 A1 | 6/2003 | Jacques | |
| 2003/0163033 A1 | 8/2003 | Dekker | |
| 2004/0215095 A1 * | 10/2004 | Lee | A61B 5/14551 |
| | | | 600/529 |
| 2005/0070775 A1 | 3/2005 | Chin et al. | |
| 2005/0215913 A1 * | 9/2005 | Lee | A61B 5/02416 |
| | | | 600/500 |
| 2005/0281439 A1 | 12/2005 | Lange | |
| 2006/0074322 A1 | 4/2006 | Nitzan | |
| 2006/0264767 A1 | 11/2006 | Shennib | |
| 2007/0142720 A1 | 6/2007 | Ridder et al. | |
| 2007/0191725 A1 | 8/2007 | Nelson | |
| 2008/0146954 A1 | 6/2008 | Bojovic et al. | |
| 2008/0208069 A1 | 8/2008 | John et al. | |
| 2008/0214961 A1 | 9/2008 | Matsumoto et al. | |
| 2008/0221419 A1 | 9/2008 | Furman | |
| 2008/0255433 A1 | 10/2008 | Prough et al. | |
| 2009/0024011 A1 * | 1/2009 | Huiku | A61B 5/14551 |
| | | | 600/323 |
| 2009/0163821 A1 | 6/2009 | Caros et al. | |
| 2009/0247848 A1 | 10/2009 | Baker, Jr. | |
| 2010/0016694 A1 * | 1/2010 | Martin | A61M 16/0051 |
| | | | 600/324 |
| 2010/0179438 A1 | 7/2010 | Heneghan et al. | |
| 2010/0192952 A1 * | 8/2010 | Melker | A61B 5/6817 |
| | | | 128/204.23 |
| 2010/0217144 A1 | 8/2010 | Brian | |
| 2010/0298656 A1 | 11/2010 | McCombie et al. | |
| 2010/0312079 A1 | 12/2010 | Larsen et al. | |
| 2010/0324384 A1 | 12/2010 | Moon et al. | |
| 2011/0060200 A1 | 3/2011 | Bernreuter | |
| 2011/0066051 A1 | 3/2011 | Moon et al. | |
| 2011/0077486 A1 | 3/2011 | Watson et al. | |
| 2011/0082355 A1 | 4/2011 | Eisen et al. | |
| 2011/0201946 A1 | 8/2011 | Turcott | |
| 2011/0224564 A1 | 9/2011 | Moon et al. | |
| 2011/0257551 A1 | 10/2011 | Banet et al. | |
| 2012/0190944 A1 | 7/2012 | Thaveeprungsriporn et al. | |
| 2012/0238834 A1 | 9/2012 | Hornick | |
| 2013/0231947 A1 | 9/2013 | Shusterman | |
| 2013/0296665 A1 | 11/2013 | Kassim et al. | |
| 2013/0296666 A1 | 11/2013 | Kumar et al. | |
| 2013/0296673 A1 | 11/2013 | Thaveeprungsriporn et al. | |
| 2013/0310700 A1 | 11/2013 | Wiard et al. | |
| 2013/0338460 A1 | 12/2013 | He et al. | |
| 2014/0043164 A1 | 2/2014 | Eschelman et al. | |
| 2014/0088449 A1 | 3/2014 | Nearing et al. | |
| 2014/0142445 A1 | 5/2014 | Banet et al. | |
| 2014/0155705 A1 | 6/2014 | Papadopoulos et al. | |
| 2014/0206948 A1 * | 7/2014 | Romem | A61B 5/0022 |
| | | | 600/301 |
| 2014/0257122 A1 | 9/2014 | Ong et al. | |
| 2014/0275888 A1 | 9/2014 | Wegerich et al. | |
| 2014/0278229 A1 | 9/2014 | Hong et al. | |
| 2015/0109125 A1 | 4/2015 | Kaib et al. | |
| 2015/0148622 A1 | 5/2015 | Moyer et al. | |
| 2015/0157220 A1 | 6/2015 | Fish et al. | |
| 2015/0157262 A1 | 7/2015 | Schuessler | |
| 2015/0196257 A1 * | 7/2015 | Yousefi | A61B 5/024 |
| | | | 600/324 |
| 2015/0265161 A1 | 9/2015 | Hernandez et al. | |
| 2015/0272510 A1 | 10/2015 | Chin | |
| 2015/0305689 A1 | 10/2015 | Gourmelon et al. | |
| 2015/0313484 A1 | 11/2015 | Burg et al. | |
| 2015/0320328 A1 | 11/2015 | Albert | |
| 2015/0332012 A1 | 11/2015 | Edelson et al. | |
| 2015/0342538 A1 | 12/2015 | St. Pierre et al. | |
| 2015/0366469 A1 | 12/2015 | Harris et al. | |
| 2015/0366492 A1 * | 12/2015 | De Haan | A61B 5/7214 |
| | | | 600/323 |
| 2015/0366518 A1 * | 12/2015 | Sampson | A61B 5/7221 |
| | | | 600/301 |
| 2016/0000376 A1 | 1/2016 | Murray et al. | |
| 2016/0022220 A1 * | 1/2016 | Lee | A61B 5/721 |
| | | | 600/479 |
| 2016/0089033 A1 | 3/2016 | Saponas et al. | |
| 2016/0093205 A1 | 3/2016 | Boyer | |
| 2016/0120434 A1 | 5/2016 | Park et al. | |
| 2016/0183846 A1 | 6/2016 | Derkx | |
| 2016/0270668 A1 | 9/2016 | Gil | |
| 2016/0270677 A1 | 9/2016 | Lin | |
| 2016/0360974 A1 | 12/2016 | Lange | |

(56) References Cited

U.S. PATENT DOCUMENTS

| | | |
|---|---|---|
| 2016/0360986 A1 | 12/2016 | Lange |
| 2016/0361003 A1 | 12/2016 | Lange et al. |
| 2016/0361004 A1 | 12/2016 | Lange et al. |
| 2017/0014037 A1* | 1/2017 | Coppola ............. A61B 5/6898 |
| 2017/0156593 A1 | 6/2017 | Ferber et al. |
| 2017/0202459 A1 | 7/2017 | Cao |
| 2017/0258406 A1 | 9/2017 | Lange |
| 2018/0098705 A1 | 4/2018 | Chaturvedi et al. |
| 2018/0132794 A1 | 5/2018 | Lange |
| 2018/0247713 A1 | 8/2018 | Rothman |
| 2019/0015014 A1 | 1/2019 | Lange |
| 2021/0145310 A1 | 5/2021 | Lange |

FOREIGN PATENT DOCUMENTS

| | | |
|---|---|---|
| CN | 107920786 A | 4/2018 |
| CN | 107920786 B | 12/2020 |
| EP | 2430975 A1 | 3/2012 |
| EP | 3307146 | 4/2018 |
| EP | 3307150 | 4/2018 |
| EP | 3307162 | 4/2018 |
| EP | 3493734 A1 | 6/2019 |
| EP | 3307146 B1 | 11/2020 |
| EP | 3731744 A1 | 11/2020 |
| EP | 3849407 A1 | 7/2021 |
| WO | WO0047108 A1 | 8/2000 |
| WO | WO2001015597 | 3/2001 |
| WO | WO2006048701 A2 | 5/2006 |
| WO | WO2014022906 A1 | 2/2014 |
| WO | WO2015047015 A1 | 4/2015 |
| WO | WO2015070030 A1 | 5/2015 |
| WO | WO2015197383 A1 | 12/2015 |
| WO | WO2016110804 A1 | 7/2016 |
| WO | WO2016199121 A1 | 12/2016 |
| WO | WO2016199122 A1 | 12/2016 |
| WO | WO2016199123 A1 | 12/2016 |
| WO | WO2016199124 A1 | 12/2016 |
| WO | WO2017141131 A1 | 8/2017 |
| WO | WO2017158585 A1 | 9/2017 |
| WO | WO2018025257 A1 | 2/2018 |
| WO | WO2018085563 A1 | 5/2018 |
| WO | WO2019130296 A1 | 7/2019 |
| WO | WO2020053858 A1 | 3/2020 |

OTHER PUBLICATIONS

Ye et al., "Estimation of Systolic and Diastolic Pressure using the Pulse Transit Time", International Journal of Medical, Health, Biomedical, Bioengineering and Pharmaceutical Engineering vol. 4. No. 7, 2010, pp. 303-308.

International Search Report and Written Opinion dated Jul. 11, 2016 in Patent Cooperation Treaty Application No. PCT/IL2016/050511 filed May 15, 2016, pp. 1-19.

International Search Report and Written Opinion dated Aug. 18, 2016 in Patent Cooperation Treaty Application No. PCT/IL2016/050514 filed May 15, 2016, pp. 1-20.

International Search Report and Written Opinion dated Aug. 29, 2016 in Patent Cooperation Treaty Application No. PCT/IL2016/050513 filed May 15, 2016, pp. 1-18.

Patent Cooperation Treaty Application No. PCT/IL2016/050512, "International Search Report" and "Written Opinion of the International Searching Authority," dated Sep. 18, 2016, 9 pages.

Final Office Action, dated Mar. 22, 2017, U.S. Appl. No. 14/738,636, filed Jun. 12, 2015.

Non-Final Office Action, dated May 17, 2017, U.S. Appl. No. 15/226,881, filed Aug. 2, 2016.

"International Search Report" and "Written Opinion of the International Searching Authority," Patent Cooperation Treaty Application No. PCT/IL2017/050242, dated Jun. 13, 2017, 12 pages.

Abtahi, Farhad, "Feasibility of Fetal EEG Recording," Master's Thesis, Department of Signal and System, Chalmers University of Technology, Gothenburg, Sweden, Jan. 1, 2011, 51 pages.

Richardson, Kelly et al., "Electrocardiographic damage scores and cardiovascular mortality," American Heart Journal vol. 149, No. 3, Mar. 1, 2005, pp. 458-463.

Non-Final Office Action, dated Aug. 16, 2017, U.S. Appl. No. 15/069,739, filed Mar. 14, 2016.

Non-Final Office Action, dated Sep. 5, 2017, U.S. Appl. No. 14/738,636, filed Jun. 12, 2015.

Final Office Action, dated Sep. 18, 2017, U.S. Appl. No. 15/226,881, filed Aug. 2, 2016.

Non-Final Office Action, dated Sep. 21, 2017, U.S. Appl. No. 14/738,711, filed Jun. 12, 2015.

"International Search Report" and "Written Opinion of the International Searching Authority," Patent Cooperation Treaty Application No. PCT/IL2017/050826, dated Oct. 23, 2017, 9 pages.

"Extended European Search Report," European Patent Application No. 16807014.2, dated Oct. 22, 2018, 8 pages.

"Extended European Search Report," European Patent Application No. 16807015.9, dated Jan. 21, 2019, 10 pages.

Gözde, Ateş et al., "Measuring of Oxygen Saturation Using Pulse Oximeter Based on Fuzzy Logic," Medical Measurements and Applications Proceedings (MEMEA), 2012 IEEE International Symposium, May 18, 2012, pp. 1-6.

"Extended European Search Report," European Patent Application No. 16807013.4, dated Jan. 17, 2019, 7 pages.

"International Search Report" and "Written Opinion of the International Searching Authority," Patent Cooperation Treaty Application No. PCT/IL2018/051384, dated Mar. 14, 2019, 15 pages.

"Extended European Search Report," European Patent Application No. 17836517.7, dated Feb. 25, 2020, 5 pages.

"Office Action," Chinese Patent Application No. 201680042023.6, dated Mar. 20, 2020, 10 pages.

"Office Action," European Patent Application No. 16807013.4, dated Aug. 27, 2019, 6 pages.

"International Search Report" and "Written Opinion of the International Searching Authority," Patent Cooperation Treaty Application No. PCT/IL2019/051018, dated Dec. 17, 2019, 14 pages.

"Notice of Allowance," European Patent Application No. 16807013.4, dated May 26, 2020, 7 pages.

"Office Action," European Patent Application No. 16807015.9, dated Aug. 6, 2020, 7 pages.

"Notice of Allowance", European Patent Application No. 17836517.7, dated Oct. 1, 2020, 7 pages.

"Notice of Allowance", European Patent Application No. 16807015.9, dated Mar. 9, 2021, 7 pages.

"Office Action", European Patent Application No. 16807014.2, dated Apr. 30, 2021, 6 pages.

Sam et al., "Feasibility of single-arm single-lead ECG biometrics", 22nd European Signal Processing Conference (EUSIPCO), Sep. 1, 2014, pp. 2525-2529.

"Extended European Search Report", European Patent Application No. 18897389.5, dated Aug. 4, 2021, 9 pages.

Zhang et al., "Theoretical Study on the Effect of Sensor Contact Force on Pulse Transmit Time", IEEE Transactions on Biomedical Engineering, Sep. 2007, 10 pages.

* cited by examiner

MONITORING HEALTH STATUS OF PEOPLE SUFFERING FROM CHRONIC DISEASES

CROSS-REFERENCE TO RELATED APPLICATIONS

The present application is related to U.S. patent application Ser. No. 14/738,636 titled "Wearable Device Electrocardiogram" filed on Jun. 12, 2015 and U.S. patent application Ser. No. 14/738,711 titled "Pulse Oximetry" filed on Jun. 12 2015. The subject matter of the aforementioned applications is incorporated herein by reference for all purposes.

FIELD

The present application relates to systems and methods for monitoring health status of people suffering from chronic diseases.

BACKGROUND

It should not be assumed that any of the approaches described in this section qualify as prior art merely by virtue of their inclusion in this section.

Monitoring chronic diseases, which includes measuring medical parameters, is central for providing appropriate and timely treatment to patients suffering from such chronic diseases as chronic heart failure, cardiac arrhythmia, chronic obstructive pulmonary disease, asthma, and diabetes. Traditionally, monitoring is carried out and measurements are taken while a patient is hospitalized or in other clinical settings. An appropriate treatment regimen can be based on these measurements, and thus it is highly beneficial to monitor medical parameters of the patient after the patient is released from the hospital. Therefore, the patient can be asked to visit the hospital or clinic periodically for monitoring, and adjustment of treatment, if necessary. However, most often, no measurements are carried out between visits, usually due to the need for trained examiners and medical devices. This is unfortunate, because between visits the chronic disease from which the patient suffers can worsen and result in emergency treatment and hospitalization. Furthermore, after receiving repeated courses of emergency hospital treatment, the patient's health condition may degrade and never return to the pre-hospitalization level. Therefore, a technology that allows for at-home measurements can be essential to managing chronic diseases or even saving a patient's life. Early warnings of worsening conditions associated with chronic diseases may prevent unnecessary hospitalizations by providing a preventive treatment and, as a result, reduce financial and human costs of the hospitalization and treatment.

Currently there are no user-friendly devices for continuous non-intrusive measurements of medical parameters of patients at their home or working environment. In some cases, patients with severe symptoms can be monitored at home while staying in bed. However, devices for taking measurements of bedridden patients are generally not suitable for chronic patients which, with timely treatment, should be able to maintain a high quality normal life.

Some existing mobile devices can provide functionalities for tracking people's physical activity. Such devices can measure a pulse rate and the distance a person walks or runs, calculate burned calories, and so forth. Some of these existing devices are designed as or are part of a watch, a bracelet, and a wristband. However, these devices are primarily designed for healthy people for the monitoring of physical exercise and not for chronically ill people.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

According to one embodiment of the present disclosure, a system for monitoring health status of a patient is provided. The system can be embedded in a wearable device, and includes at least one sensor. The wearable device is configured to continuously collect, via the sensor or sensors, data from a single place on the body of a patient. The wearable device can store or transmit the sensor data for subsequent processing and analysis to obtain medical parameters. The sensor data can be processed to receive at least electrocardiogram (ECG) data and photoplethysmogram (PPG) data. The ECG data and PPG data can be analyzed to obtain the medical parameters. The medical parameters can be associated with at least one chronic disease. The medical parameters can be analyzed to track changes in the medical parameters over time. Based at least partially on the changes in the medical parameters, a dynamic profile of the chronic disease can be determined, which can be used to monitor disease progression or remission.

In some embodiments, the sensors include at least one of the following: an optical sensor, an electrical sensor, and a motion sensor. The wearable device includes a wristband operable to be placed around a wrist of the patient. The wristband can include sensors in a dedicated sensor area. The sensor area can be arranged to cover at least the radial artery of the patient. In other embodiments, the wearable device can be worn at a wrist, ankle, chest, neck, and positioned at other sites of a human body.

The medical parameters that are monitored include but are not limited to at least one of $SpO_2$ oxygen saturation, tissue oxygen saturation, cardiac output, vascular resistance, pulse rate, blood pressure, respiration, and motion data.

In some embodiments, the chronic disease might be at least one of the following: congestive heart failure, hypertension, arrhythmia, asthma, chronic obstructive pulmonary disease, hypoglycemia, hyperglycemia, sleep apnea, and Parkinson's disease.

The determination of the progression or remission includes estimation of a deviation or divergence of at least one of the medical parameters from expected medical parameters. The expected medical parameters are based on individual historical medical parameters of the patient as well as on established or theoretical medical knowledge.

If the deviation of the at least one medical parameter is larger than a pre-determined deviation value, the wearable device may be further configured to alert at least one of the following: the patient, a doctor, a relative of the patient, and a caretaker of the patient. In certain embodiments, the wearable device is operable to advise the patient to contact a medical professional.

If the deviation of the at least one medical parameter is larger than a pre-determined value; the wearable device may be further configured to provide an alert message to the patient. The alert message can include an advisory to take medicine. In certain embodiments, the wearable device is further configured to determine, based on changes in the medical parameters, that the patient has taken the medicine.

In various embodiments, when the deviation of the medical parameter is less than a pre-determined value, the wearable device is configured to repeatedly message the patient to assure the patient of a normal health condition.

In certain embodiments, when the deviation of the medical parameter is less than a pre-determined value, the wearable device is configured to repeatedly provide a sensory stimulus such as sound or vibration to the patient to assure that the patient of a normal health condition.

In further embodiments, the wearable device is communicatively coupled to a mobile device. The mobile device can be configured to receive the sensor data from the wearable device, analyze the sensor data to provide medical parameters, and process the medical parameters to provide to the patient at least one report regarding the health condition of the patient.

The mobile device may be communicatively coupled to a cloud-based computing resource. The cloud-based computing resource is configured to receive the sensor data and/or the medical parameters from the mobile device for further analysis and provide at least one application for generating, based on the sensor data and/or the medical parameters, at least one report regarding the health status of the patient.

According to another aspect of the present disclosure, a method for monitoring a patient's health status is provided. The method can include continuously collecting, via sensors, physiological data from a single place on the body of the patient. The method can allow processing the sensor data to obtain at least ECG data and PPG data. At least one of the ECG data and PPG data are analyzed to obtain medical parameters associated with at least one chronic disease. The method can include analyzing the medical parameters to track changes in the medical parameters over time. The method can include determining, based at least partially on the changes in the medical parameters, a dynamic profile of at least one chronic disease. In some embodiments, the sensors are associated with a wearable device. The wearable device can be placed around a wrist of the patient. The sensors can be arranged to cover at least a radial artery and/or nearby skin tissue of the patient.

According to another example embodiment of the present disclosure, the steps of the method for monitoring a patient's health status are stored on a non-transitory machine-readable medium comprising instructions, which when implemented by one or more processors perform the recited steps.

Other example embodiments of the disclosure and aspects will become apparent from the following description taken in conjunction with the following drawings.

BRIEF DESCRIPTION OF THE DRAWINGS

Embodiments are illustrated by way of example and not limitation in the figures of the accompanying drawings, in which like references indicate similar elements and in which.

DETAILED DESCRIPTION

The following detailed description includes references to the accompanying drawings, which form a part of the detailed description. The drawings show illustrations in accordance with exemplary embodiments. These exemplary embodiments, which are also referred to herein as "examples," are described in enough detail to enable those skilled in the art to practice the present subject matter. The embodiments can be combined, other embodiments can be utilized, or structural, logical and electrical changes can be made without departing from the scope of what is claimed. The following detailed description is, therefore, not to be taken in a limiting sense, and the scope is defined by the appended claims and their equivalents.

The present disclosure provides systems and methods for monitoring health status in people suffering from chronic diseases. Embodiments of the present disclosure can allow measuring medical parameters of a patient in a non-intrusive manner while, for example, the patient is at home, at work, outdoors, traveling, and at other stationary or mobile environments. Some example embodiments can provide for a wearable device (e.g., a wristband, a watch, or a bracelet) that includes sensors configured to measure medical parameters such as, for example, blood pressure, heart rate, blood oxygen saturation, respiration, and the like. The measurements can be taken during daytime and nighttime for days, weeks, months, and years. The medical parameters can be analyzed to determine trends in the medical parameters and to determine whether the severity of the patient's chronic disease (e.g., a heart disease, diabetes, lung disease, and so on) worsens or improves. Embodiments of the present technology may facilitate a rapid reaction to provide an appropriate and timely treatment for the patient. The early treatment may allow taking timely measures to avoid worsening of the patient's condition to the point of requiring an emergency hospitalization and associated expensive medical treatment.

According to various example embodiments, a method for monitoring health status of people suffering from chronic diseases includes continuously collecting sensor data from a single place on the body of a patient. The method can further include processing the sensor data to obtain at least electrocardiogram (ECG) data and photoplethysmogram (PPG) data. The method may include analyzing at least one of the ECG data and the PPG data to obtain medical parameters associated with at least one chronic disease. The method can allow detecting changes in the medical parameters over time. The method includes determining, based at least partially on the changes in the medical parameters, a dynamic profile of the at least one chronic disease. The method can allow, based at least on the progression or remission, providing at least one message to the patient.

Figure 1:
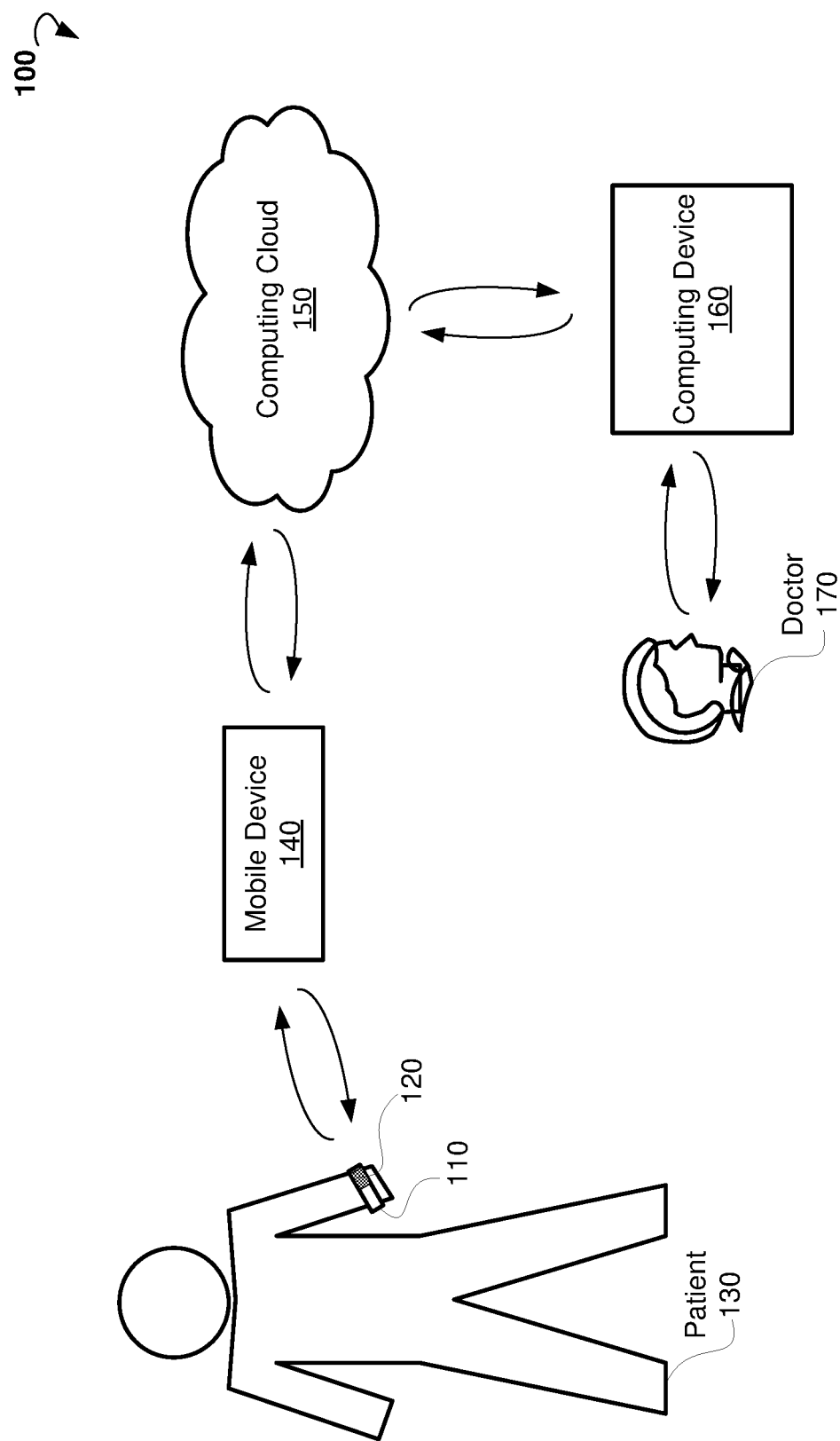
FIG. 1 is a block diagram showing an example system for monitoring the health status of a chronically ill patient.

Referring now to FIG. 1, an example system 100 for monitoring a patient's health status is shown. The system 100 includes at least a wearable device 110. The wearable device includes sensors 120. In some embodiments, the wearable device 110 is worn by a patient 130, for example on a wrist, for an extended period of time. The wearable device 110 can be carried out as a watch, a bracelet, a wristband, and the like.

The wearable device 110 is operable to constantly collect, via sensors 120, sensor data from a patient 130. In some embodiments, based on the sensor data, the wearable device 110 is operable to obtain medical parameters associated with the patient 130. The medical parameters can be analyzed to obtain changes (trends) in medical parameters over time. Based on the changes, one or more conclusions regarding severity of one or more chronic disease can be obtained. The wearable device is operable to send messages regarding the current health status to the patient, a relative, a caretaker of the patient, or a doctor treating the patient. The patient can be advised to see a doctor and/or take medicine. In some embodiments, the wearable device 110 analyzes the medical parameters to determine whether the patient has taken the medicine and to provide further advice to the patient.

In various embodiments, the system 100 includes a mobile device 140. The mobile device 140 can be communicatively coupled to the wearable device 110. In various embodiments, the mobile device 140 is operable to communicate with the wearable device 110 via a wireless connection. The mobile device 140 can include a mobile phone, a smart phone, a phablet, a tablet computer, a notebook, and so forth. The mobile device 140 can be operable to receive the sensor data and medical parameters from the mobile device 110. In certain embodiments, the mobile device is operable to perform analysis of the received sensor data and medical parameters and to provide the patient with a report regarding current health status. In various embodiments, the mobile device 140 runs one or more applications that provide, via a graphical display system, charts and graphics concerning medical parameters of the patient.

In some embodiments, the mobile device 140 is operable to determine the severity of the health status resulting from the chronic disease from which the patient suffers and provide the patient with advice to see a medical professional or to take medicine. An alert message regarding the health status of the patient can be sent to a doctor, a relative, or caretaker of the patient.

In further embodiments, the system 100 may include a cloud-based computing resource 150. In some embodiments, the computing cloud 150 includes one or more server farms/clusters comprising a collection of computer servers and is co-located with network switches and/or routers. In certain embodiments, the mobile device 140 is communicatively coupled to the computing cloud 150. The mobile device 140 can be operable to send the sensor data and medical parameters to the computing cloud 150 for further analysis. The computing cloud 150 is operable to store historical data concerning patient health status including sensor data and medical parameters collected over days, weeks, months, and years. The computing cloud can be operable to run one or more applications and to provide reports regarding health status of the patient. A doctor 170 treating the patient may access the reports, for example via computing device 160, using the Internet or a secure network. In some embodiments, the results of the analysis of the medical parameters can be sent back to the mobile device 140.

The severity of the health status resulting from a chronic disease can be estimated by computing a deviation or divergence from normal medical parameters of one or more medical parameters being measured at the moment. The normal medical parameters can be specific to the patient and can be derived based on historical data concerning the patient's health status recorded over an extended time period. If the deviation in the medical parameters becomes sufficiently large, the patient can be advised, via a message to the mobile device 140, to take medicine or contact a doctor. In some situations, when the deviation becomes substantial, an alert message can be sent by the mobile device 140 and/or the wearable device 110 to a relative, a doctor, or a caretaker of the patient.

It may be desirable for the patient to be assured that the current medical parameters are within an acceptable deviation of the normal medical parameters. For example, when the current medical parameters are normal, the wearable device 110 and/or mobile device 140 can be operable to periodically alert the patient using a pleasant sound. The signal can be provided, for example, every 30 minutes, once every hour, and the like. In certain embodiments, when the medical parameters are within normal values, the mobile device 140 may provide a text message assuring the patient of normal conditions. A haptic feedback component can be used to alert the patient to a health condition, to warn the patient about a specific event concerning treatment of a chronic disease, to remind the patient to take a medicine, if the patient has failed to take the medicine within a predetermined period of time, and so forth. The wearable device 110 may include a haptic feedback functionality for providing the patient with haptic feedback, for example, a tap-in device, to apply a force or vibration to skin of the patient. In further embodiments, the haptic alert can be provided by the mobile device 140. The mobile device can vibrate when the mobile device in a pocket of the patient or when the mobile device is located on a surface (e.g., a table).

Figure 2:
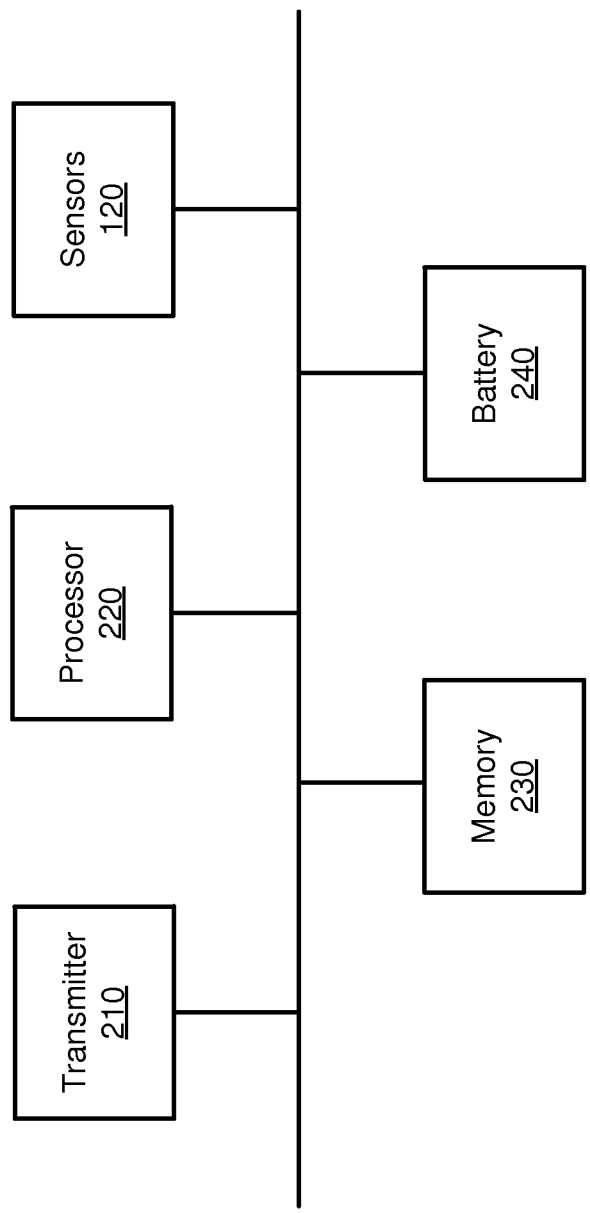
FIG. 2 is a block diagram showing components of an example device for monitoring the health status of a chronically ill patient.

FIG. 2 is a block diagram illustrating components of wearable device 110, according to an example embodiment. The example wearable device 110 includes sensors 120, a transmitter 210, processor 220, memory 230, and a battery 240. The wearable device 110 may comprise additional or different components to provide a particular operation or functionality. Similarly, in other embodiments, the wearable device 110 includes fewer components that perform similar or equivalent functions to those depicted in FIG. 2.

The transmitter 210 is configured to communicate with a network such as the Internet, a Wide Area Network (WAN), a Local Area Network (LAN), a cellular network, and so forth, to send a data stream, for example sensor data, medical parameters, and messages concerning the health condition of a patient.

The processor 220 can include hardware and/or software, which is operable to execute computer programs stored in memory 230. The processor 220 can use floating point operations, complex operations, and other operations, including processing and analyzing sensor data.

In some embodiments, the battery 240 is operable to provide electrical power for operation of other components of the wearable device 110. In some embodiments, the battery 240 is a rechargeable battery. In certain embodiments, the battery 240 is recharged using inductive charging technology.

Figure 3:
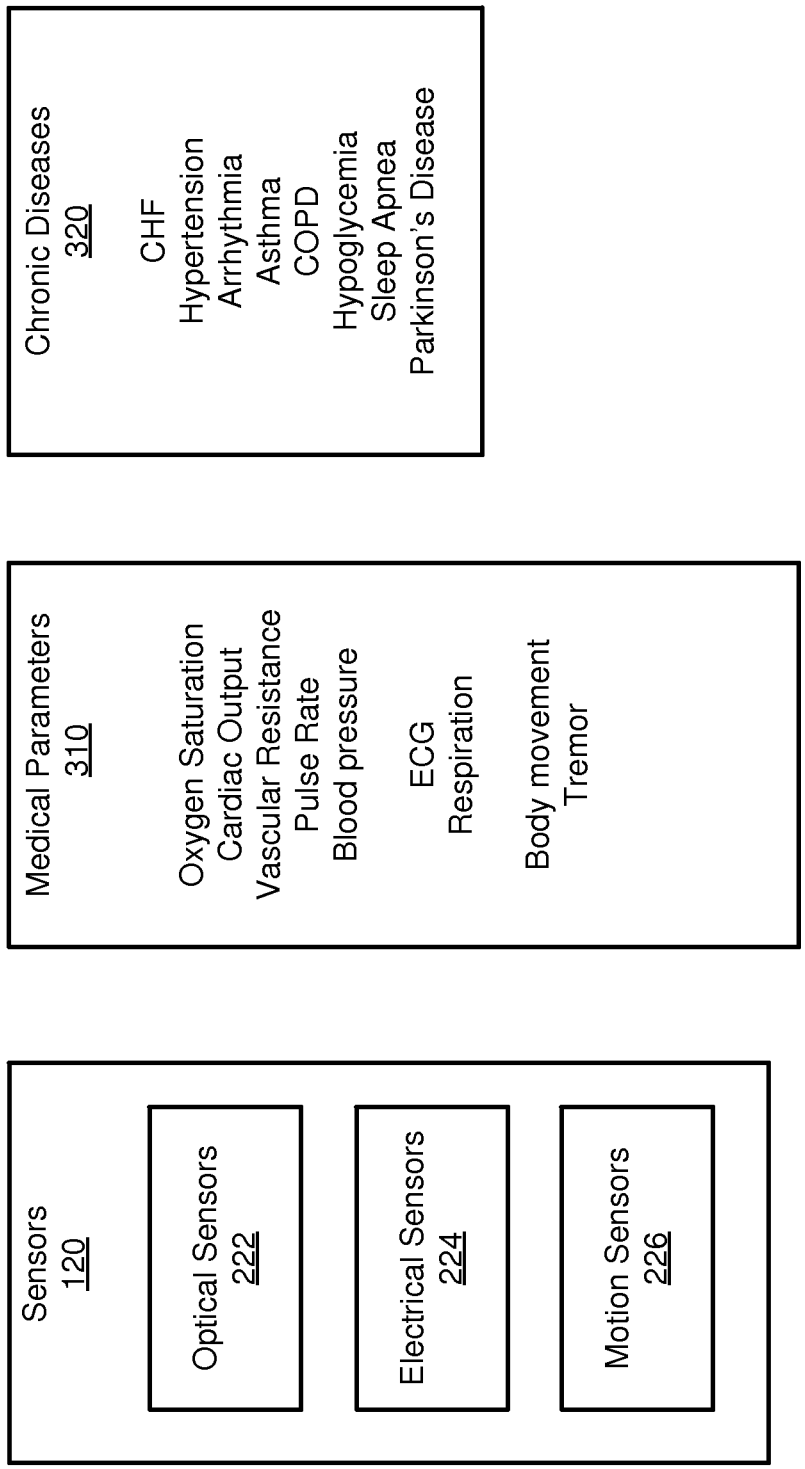
FIG. 3 is a block diagram illustrating example sensors, example medical parameters, and example chronic diseases.

FIG. 3 is a block diagram showing a list of example sensors 120, a list of example medical parameters 310, and a list of example chronic diseases 320. In various embodiments, the sensors 120 include optical sensors 222, electrical sensors 224, and motion sensors 226. The medical parameters 310, determined based on the sensor data, include, but are not limited to, $SpO_2$ oxygen saturation, tissue oxygen saturation, cardiac output, vascular resistance, pulse rate, blood pressure, respiration, electrocardiogram (ECG) data, and motion data. The chronic diseases 320, the progression of which can be tracked based on changes of the medical parameters, include but are not limited to congestive heart failure (CHF), hypertension, arrhythmia, asthma, chronic obstructive pulmonary disease (COPD), hypoglycemia, sleep apnea, and Parkinson's disease.

The optical sensors 222 are operable to measure medical parameters associated with blood flow in an artery (for example, radial artery) using changing absorbance of light at different wavelengths in arterial blood and skin. The optical sensor can determine multiple medical parameters, including but not limited to: $SpO_2$ oxygen saturation, cardiac output, vascular resistance, pulse rate, and respiration. Based on the measurements obtained from optical sensors, abnormal cardiac rhythms (for example, atrial fibrillation, rapid rhythms and slow rhythms) can be detected.

In some embodiments, respiration can be derived from a sinus arrhythmia waveform. The sinus arrhythmia waveform can be obtained based on intervals between subsequent heart beats (RR intervals) measured by the optical sensors using the fact that the rhythm of the heart beats is modulated by human breathing.

The electrical sensors 224 can be operable to obtain electrocardiographic (ECG) activity data of the patient. The ECG activity data includes a characteristic electrically-derived waveform of a heart activity. The ECG data can include a number of components, whose characteristics (timing, amplitude, width, and so forth), alone or in combination, can provide a picture of cardiac and overall health. The ECG data is typically derived by measurements from one or more sets of leads (groups of electrodes comprising grounded circuits), such that the exact characteristics of the resulting waveforms is a function of the electrical and spatial vectors of the electrode positions relative to the heart. While the details of interpretation of the ECG data are too involved to describe succinctly in this disclosure, consideration of each of the component parameters can indicate health status, physical or psychological stress, or trends of disease conditions. Various cardiovascular parameters can be extracted from the ECG alone (such as a heart rate for example), or in combination with other physiological measurements.

ECG-like components can also be obtained, or re-constructed, through other methods of physiological measurements, such as mechano-cardiography, for example.

According to example embodiments of present disclosure, ECG of the patient can be measured via the electrical sensors 224. Since measurements are taken from a wrist of the patient, electrodes of the electrical sensors 224 should be located very close to each other on a wearable device. Therefore the ECG data may contain noise. Averaging of several subsequent intervals of the ECG data between heart beats can be used to cancel out noise in ECG data. To determine intervals between two subsequent heart beats, the pulse wave as measured by optical sensors 222 can be used as a reference. In some embodiments, an arrhythmia analysis can be carried out using the ECG data and data concerning cardiac output and pulse rate.

In some embodiments, motion sensors 226 include an accelerometer, gyroscope, and Inertial Measurement Unit (IMU). The motion data obtained via motion sensors 226 can provide parameters of body movement and tremor. The motion data can allow tracking the progression or remission of a motor disease, Parkinson's disease, and physical condition of the patient. In some embodiments, the motion data can be analyzed to determine whether the patient is likely to fall. In some embodiments, the motion data can be analyzed in time domain and frequency domain. By tracking amplitudes of movement of the patient it can be determined if the patient's movements become slower (i.e., the patient becomes sluggish) or the patient is not moving at all.

Figure 4B:
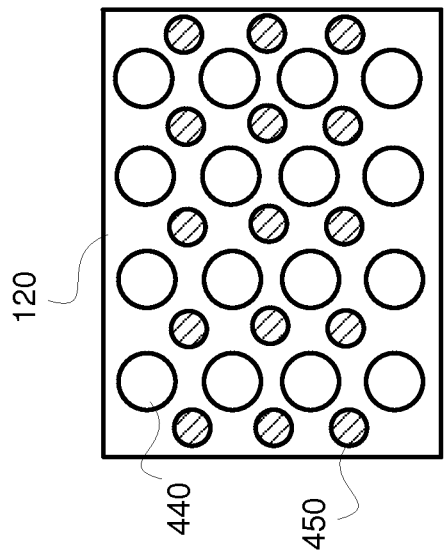
FIGS. 4A and 4B are schematic diagrams illustrating an example device for monitoring health status of a chronically ill patient.
Figure 4A:
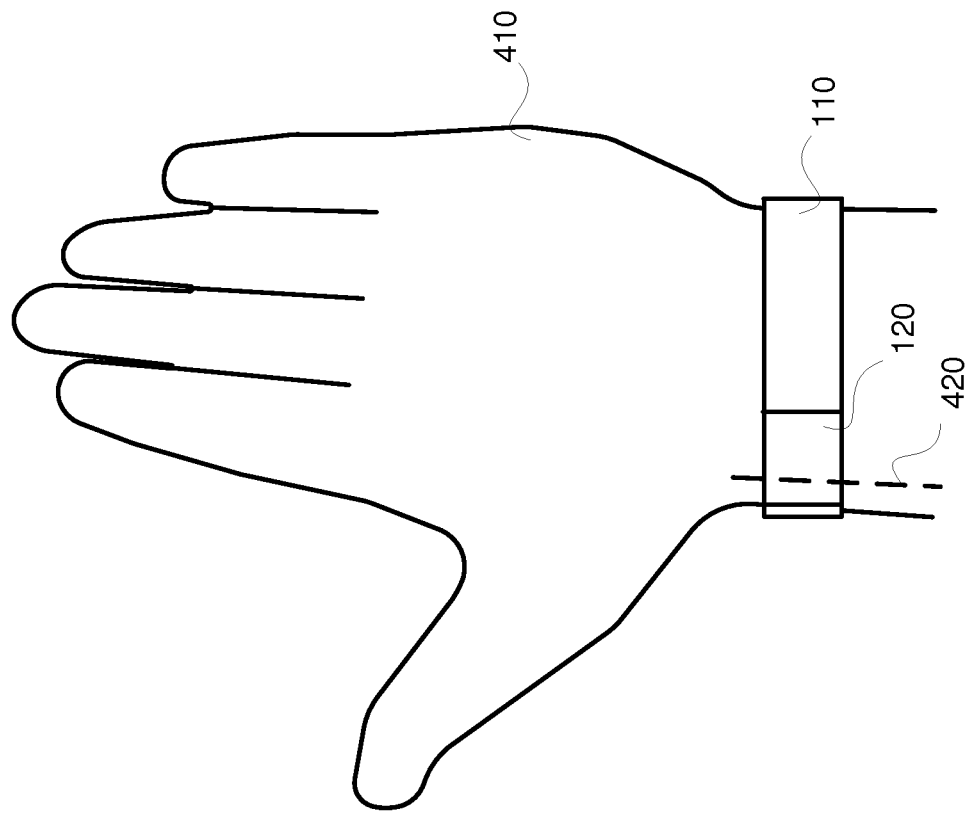

FIG. 4A is a schematic diagram illustrating an example wearable device 110. The wearable device 110 can be carried out as a watch or, a bracelet, or a wristband. The wearable device 110 can include sensors 120. The wearable device 110 can be placed around a wrist of patient's hand 410 in such a way that sensors 120 are located above and as close as possible to the radial artery 420. The radial artery is located right beneath the skin, thereby allowing measurements of oxygen saturation, heart rate, cardiac output, and other parameters by optical sensors using pulse oximetry methods.

Oxygen saturation is the relative proportion (typically expressed as percentage) of oxygen dissolved in blood, as bound to hemoglobin, relative to non-oxygen-bound hemoglobin. Oxygen saturation is important in clinical monitoring of surgical anesthesia, and in monitoring and assessment of various clinical conditions such as the COPD and asthma. In healthy individuals, oxygen saturation is over 95%. Direct measurement can be made from arterial blood sample, but drawing blood is an invasive procedure, and, except for a few controlled environments (e.g. during a surgery) cannot be easily performed continuously. Pulse oximetry can yield a quantity called $SpO_2$ (saturation of peripheral oxygen), an accepted estimate of arterial oxygen saturation, derived from optical characteristics of blood using transmission of light through a thin part of a human body, for example, a fingertip or an earlobe (in the most common transmissive application mode). Reflectance pulse oximetry can be used to estimate $SpO_2$ using other body sites. The reflectance pulse oximetry does not require a thin section of the person's body and is therefore can be suited to more universal application such as the feet, forehead and chest, but it has some serious issues due to the light reflected from non-pulsating tissues.

In some embodiments, the wearable device 110 includes self-adjusting mechanical catches to allow positioning the sensors 120 above the radial artery 420 by using the wrist bones as a physical reference and support.

In other embodiments, as shown in FIG. 4B, the sensors 120 include multiple light sensors 440 (photoelectric cells), to measure the reflected light, and multiple light transmitters 450 (for example, Light Emission Diodes (LEDs)). The number and location of the light sensors and light transmitters can be chosen such that in case of an accidental displacement of the wearable device, at least one of the light sensors is still located sufficiently close to the radial artery. In some embodiments, when measuring the light reflected from the skin and radial artery, a signal from those photoelectric cells that provides the strongest or otherwise determined best output can be selected for further processing in order to obtain medical parameters using methods of pulse (reflectance) oximetry. In certain embodiments, the wearable device 110 is configured to apply a pre-determined amount of pressure to the wrist each time the user wears the wearable device to allow the same conditions for the reflection of the light from the skin.

In other embodiments, when oxygen saturation cannot be measured directly from arterial blood, an indirect measurement can be performed by tracking tissue oxygen saturation. The measurement of oxygen saturation is commonly used to track progression of heart diseases or lung disease. When heart or lungs are not functioning properly, the saturation of oxygen drops in both arterial blood and tissue around the artery. Therefore, tissue oxygen saturation can be measured by sensing the skin color near the radial artery. For example, if the wearable device 110 moves so that sensors 120 are not covering the radial artery, measurements of tissue saturation near the radial artery can be used as a backup to provide values for oxygen saturation. In certain embodiments, the oxygen saturation and tissue saturation can be measured simultaneously. In some embodiments, the oxygen saturation and tissue saturation can be measured using the same optical sensor.

In some embodiments, a combination of ECG and pulse oximetry can be used to determine cardiac output. Cardiac Output (CO, Q, or Qc) is a volume of blood pumped by the ventricles of the heart per unit time, typically expressed as milliliters per minute (ml/min). The cardiac output can be directly derived from other cardiac parameters, namely as the product of stroke volume (SV, the blood volume output of the heart with each beat), and the heart rate (HR), that is, CO=SV*HR. Clinically, the cardiac output is an indicator of the sufficiency of blood supply. In healthy individuals at rest, CO is about 5 or 6 liters of blood per minute. During strenuous activity, CO can increase to levels more than five times the resting level. In conditions such as hypertension, valvular heart disease, congenital heart disease, arrhythmias, CO is typically reduced.

In some embodiments, a combination of ECG and pulse oximetry can be used to estimate CO directly using the equation CO=SV*HR, by least squares regression modeling of stroke volume (based either on individual direct calibration to a specific patient, or calibration to physical and clinical patient characteristics), and replacing SV by the appropriate regression expression. Specifically, pulse wave transit time, the interval between the ECG R wave peak and the pulse oximeter pulse wave foot, transformed by an appropriate regression expression, replaces SV. The CO estimate can be determined using individual heartbeat raw ECG and pulse oximetry waveform parameters, or may be a time-averaged estimate, derived from synchronized reconstructed one-handed ECG and averaged pulse oximeter readings over a specified time period. Simple changes in CO, useful in tracking individualized patient trends, can be obtained by similar means, without the necessity for absolute calibration.

In some embodiments, the wearable device 110 is operable to determine a pulse rate. The pulse rate is an indicator of a heart rate, as determined at a peripheral body site (arteries of a wrist, arm, leg, or neck). Considered as one of the vital signs, the pulse rate can be an indicator of a general health and physiological state. The pulse rate can be derived directly from any pulse-oximeter. Normal resting values can vary widely, but typically, remain within 60-100 pulsations per minute. Fluctuations in the heart rate (Heart rate variability or HRV) are normal, with higher degrees generally associated with better heart reactivity and health.

In some embodiments, the wearable device 110 is operable to determine a blood pressure (BP). The BP, another vital sign, generally refers to the intra-arterial pressure of blood at two specific stages of the heartbeat, the maximum pressure at systole (ventricular contraction) and the minimum pressure at diastole (relaxation and filling of ventricles), expressed as a delimited pair of numbers for systolic and diastolic BP respectively, in mmHg, e.g. 150/80 mmHg. The BP can be measured continuously by an invasive arterial catheter, non-invasive measurement at the arm by a stethoscope and a sphygmomanometer, or an automated cuff. A healthy adult resting BP can vary around 120/80 mmHg. High or low BPs are associated with many disease states, with long-term changes being associated with changes in the health status. Extreme short-term changes can be associated with acute disease episodes, particularly in chronically ill patients. A risk of developing a number of diseases, such as cardiovascular disease, can be associated with extreme BPs. Short-term changes in the BP can be associated with changes in physical or mental state.

According to some embodiments of present disclosure, a combination of ECG and pulse oximetry can be used to estimate systolic BP changes. The systolic BP changes can be estimated using a pulse wave transit time, the interval between the ECG R wave peak and the pulse oximeter pulse wave foot.

In certain embodiments, with a suitable calibration and individualized adjustment based on various patient characteristics, absolute estimates of the BP can be determined. The BP changes or absolute estimates can be determined using individual heartbeat raw ECG and pulse oximetry waveform parameters, or may be a time-averaged estimate, derived from synchronized reconstructed one-handed ECG and averaged pulse oximeter readings over some specified time period.

In some embodiments, the wearable device 110 is operable to determine vascular resistance. Vascular resistance is the force which opposes the flow of blood through the circulation. Typically, the systemic vascular resistance (SVR), which is the resistance of the peripheral circulation, is considered. Measurements can be expressed in several different unit systems; clinically the units are often mmHg/L/min, as SVR is a function of both blood pressure and cardiac output, that is, SVR=BP/CO. Normal values are typically within 10-20 mmHg/L/min. SVR can change as a result of various physiological stresses on the body, such as with exercise where the vascular resistance decreases, resulting in increased blood flow, or with drug or disease-related challenges.

Using measurements of ECG and pulse oximetry, the SVR can be derived as either a change or tracking score, or an absolute estimate, based on instantaneous (single heartbeat) or average BP and CO estimates.

In some embodiments, the wearable device 110 is operable to determine respiratory rate using a pulse oximetry and ECG. The respiratory rate, which is another vital sign, is typically expressed as the number of breaths per minute. Typical adult resting respiratory rate is about 16-20 breaths per minute. Extreme variations can result from physical or psychological stress. The respiratory rate is often affected in chronic disease states, particularly in pulmonary and cardiovascular disease. Extreme short-term changes may be associated with acute disease episodes, particularly in chronically ill patients.

In further embodiments, the wearable device 110 can be operable to track levels of one or more medicine in the blood of the patient 130 for a desired period of time. The level of medicine can be analyzed in combination with other blood parameters to see trends in progression or regression of chronical diseases. Based on the trends, the patient can be provided with advice to modify times for taking the medicine and/or amounts of the medicine. The patient can be warned if the level of the medicine in the blood is too high or too low. The doctor 170 view reports on the medicine levels to ensure that the medication level is within a proper range for providing effective treatment of the chronic diseases.

In some embodiments, the wearable device 110 can facilitate monitoring trends of medical parameters of the patient during a treatment. The information concerning the trends can be further used to predict a reaction of the patient to various medicines.

In some embodiments, an analysis of trends of the medical parameters can be used to predict susceptibility of the patient to local environment condition. For example, based on a weather forecast, a reaction of patient to a weather condition, pollen count, air pollution indices can be predicted. The patient can be given an advice, for example, to take a medicine in order to avoid worsening the health conditions.

In some embodiments, changes in monitored medical parameters can be correlated to certain social events, like news, or other external stimuli. The correlation can be used for determining psychological characteristics of the patient.

In some embodiments, the monitoring of medical parameters can be combined with monitoring particular habits of the patient. The habits can be determined based on movement activity. For example the following can be monitored: a number of steps during a day, times of waking up and going to sleep, daily time periods of performing physical exercises, and so forth. Based on the changes in medical parameters, the user can be advised, for example to change quantity and/or quality of certain activities.

Figure 5:
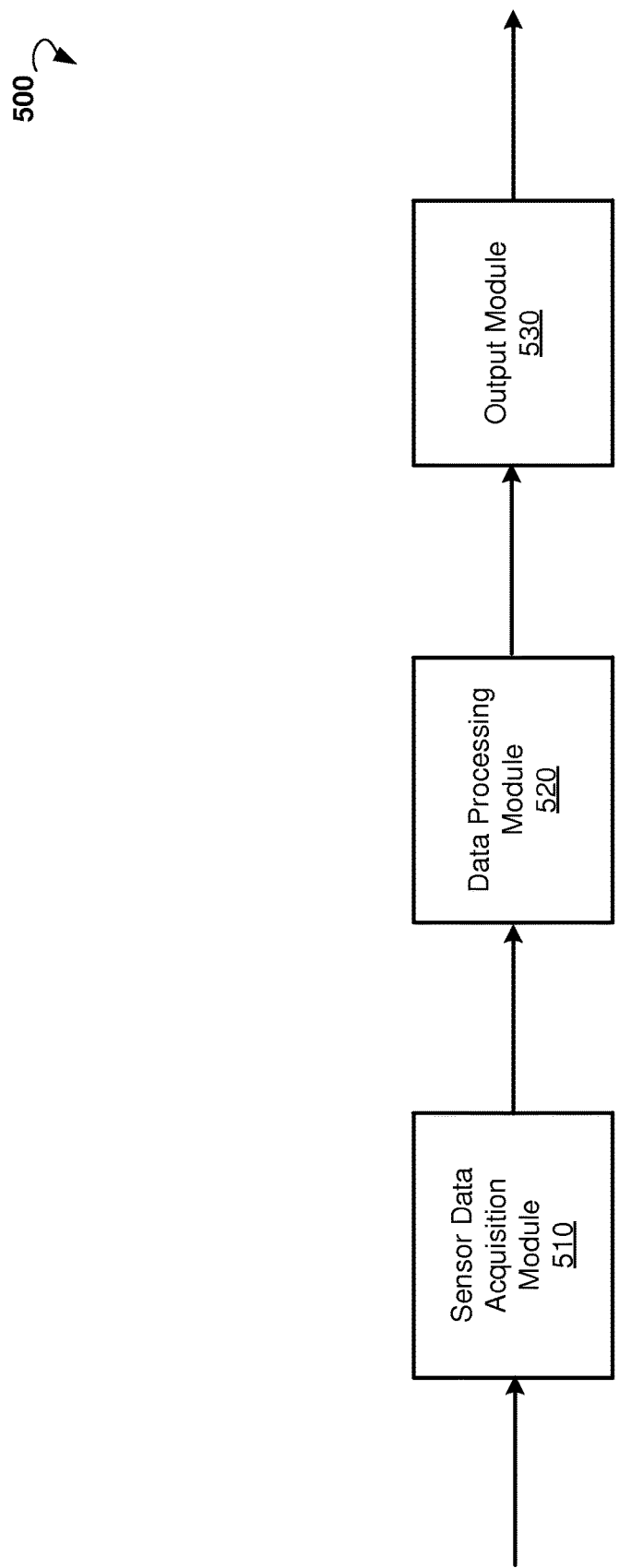
FIG. 5 is a block diagram showing an example system for monitoring a chronically ill patient.

FIG. 5 is a block diagram showing components of system 500 for monitoring health status of people suffering from chronic diseases, according to an example embodiment. The system 500 can include a sensor data acquisition module 510, a data processing module 520, and output module 530. In some embodiments, the modules 510-530 are implemented as chipsets included in the wearable device 110. In other embodiments, the modules 520 and 530 can be stored as instructions in memory of the wearable device 110, mobile device 140, or computing cloud 150, and executed by a processor.

In some embodiments, the sensor data acquisition module 510 is configured to receive and digitalize the sensor data. The sensor data acquisition module 510 can include one or more analog-to-digital converters to transform the electrical signals from sensors to digits.

In some embodiments, the data processing module 520 is configured to analyze the sensor data to obtain medical parameters associated with chronic diseases and analyze trends in medical parameters to track progression or remission of the chronic diseases.

In some embodiments, the output module 530 is configured to provide reports and alert messages regarding a health status of the patient.

Figure 6:
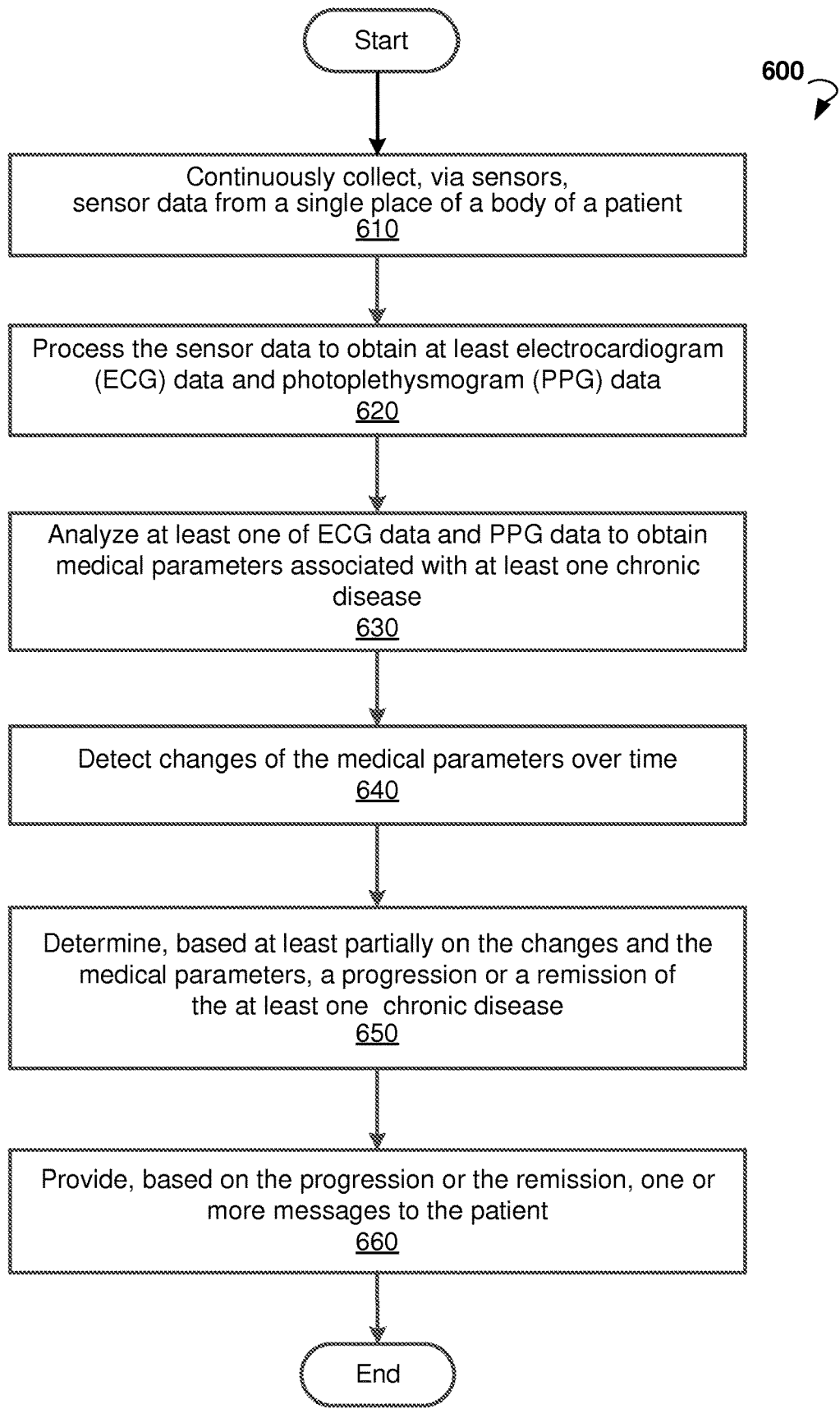
FIG. 6 is a flow chart showing steps of an example method for monitoring a chronically ill patient.

FIG. 6 is a flow chart diagram showing example method 600 for monitoring health conditions of people suffering from chronic diseases. In block 610, the method 600 incudes continuously collecting sensor data from a single place on a body of a patient. In block 620, the method 600 includes processing the sensor data to obtain at least ECG data and PPG data. In block 630, the method 600 includes analyzing at least one of the ECG data and PPG data to obtain medical parameters associated with at least one chronic disease. In block 640, the method 600 includes detecting changes in the medical parameters over time. In block 650, the method 600 includes determining, based partially on the changes and the medical parameters, a progression or a remission of the at least one chronic disease. In block 660, the method 600 includes providing, based on the progression or the remission, one or more messages to the patient.

Example 1

Asthma Severity Assessment

In some embodiments, the wearable device 110 is operable to perform assessment of asthma severity. The wearable device can be used to monitor blood SpO2 oxygen saturation, heart rate, and respiration. Measurements showing that SpO2 oxygen saturation has dropped may be indicative of an acute asthma flare-up. If an analysis of a heart rate indicates presence of tachycardia, the flare-up severity can be substantiated. Measurements of respiration can show presence of tachypnea. Tachypnea can limit speech and imply flare-up severity.

Example 2

COPD Severity Diagnostics

In some embodiments, the wearable device 110 is operable to provide COPD severity diagnostics by measuring $SpO_2$ blood oxygen saturation, respiration, and a heart rate.

A drop in blood oxygen saturation may indicate episodic worsening of COPD. If respiration shows presence of tachypnea, it substantiates worsening of COPD. If heart rate measurements show presence of tachycardia, severe worsening of COPD can be diagnosed.

Practical Considerations

One of the important considerations is how to conserve the battery power of the wearable device 110. In some embodiments, the system 100 for monitoring health conditions of people suffering from chronic diseases includes at least one additional wearable device. The additional wearable device can be identical to the wearable device 110. In some embodiments, patient 130 may wear one of the devices throughout the day and another device at nighttime. The device that is not in use at the moment can be recharged. In some embodiments, the device can be recharged using induction charging technology. In some embodiments, since both the devices are in communication with mobile device 140, the replaced device can at least partially transmit recorded information to the replacing wearable device. The information can be downloaded to the mobile device 140, and the mobile device 140 can be operable to send the information to the replacing device.

In case of a weak pulsatile signal, the non-pulsatile tissue reflection should be accounted for in order to avoid an erroneous $SpO_2$ reading. Therefore, the contribution of the non-pulsatile tissue needs to be identified and accounted for, to enable an accurate $SpO_2$ reading in such cases.

Figure 7:
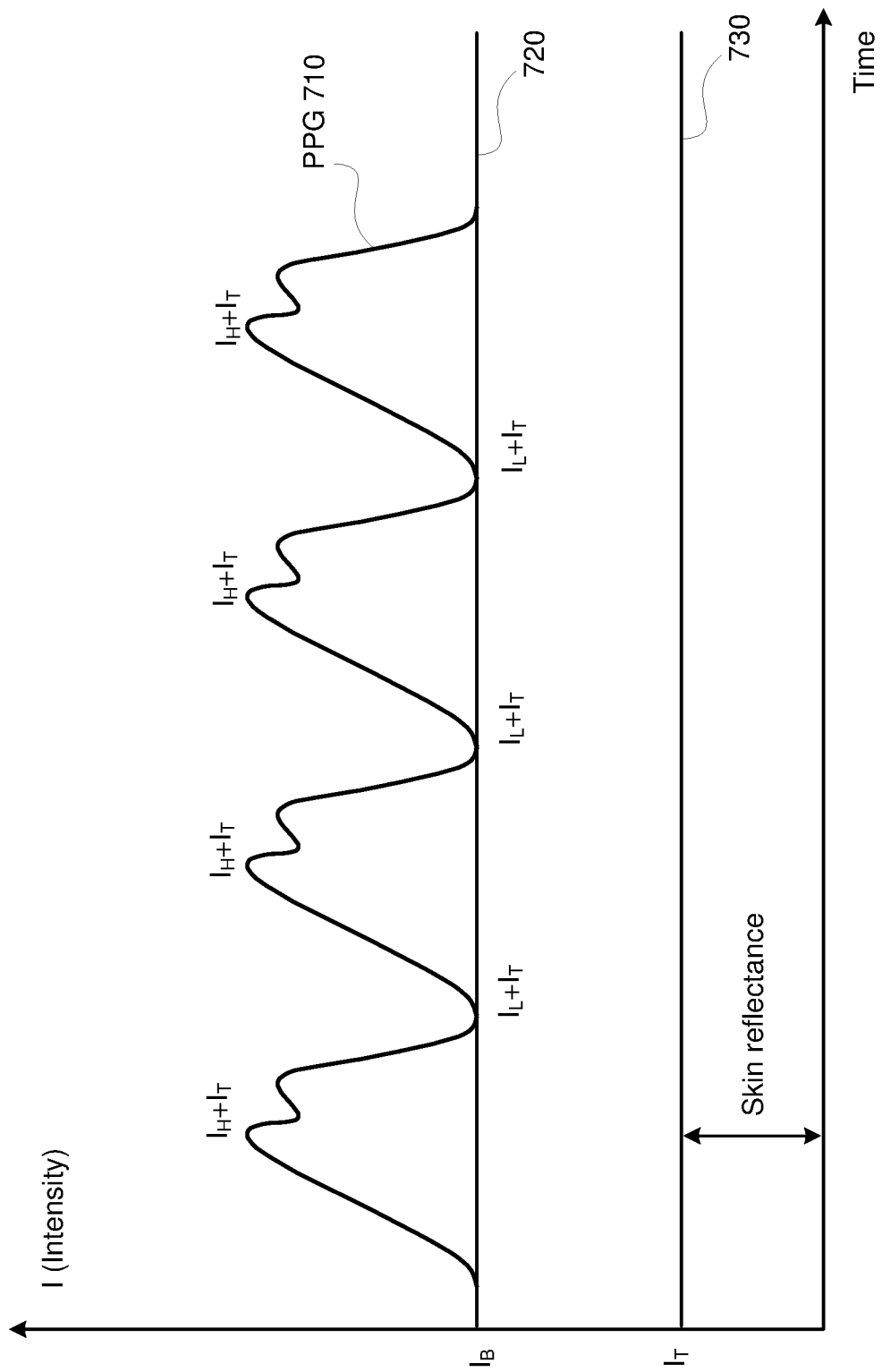
FIG. 7 shows an example plot of a photoplethysmogram (PPG).

FIG. 7 shows a plot of example PPG 710 which can be obtained with reflectance pulse oximetry. The PPG represents the intensity I of the light signal 710 (either the red signal or the infrared signal) as modulated by a human tissue mostly due to a blood flow. Both the high peaks $I_H$ and low peaks $I_L$ of the PPG 710 include a component $I_T$ due to the non-pulsatile tissue reflection. The line 720 illustrates a base intensity line for PPG and the line 730 illustrates the addition in intensity of reflected signal I due to non-pulsatile tissue (for example, skin). The following embodiments can be used to estimate the additive contribution of the non-pulsatile tissue.

Embodiment 1

According to an example embodiment of present technology, the detected signal I can be modeled as follows:

$$I = I_0(K_1 + K_2 e^{-cd})$$

While in the transmission oximetry $K_1$ is small relative to $K_2$ and thus may be neglected in both red and infrared measurements, it may not be neglected in weak signal cases such as in the general reflectance oximetry or in the low perfusion transmission oximetry.

Let us consider the following modification. Let $L^{red} > 0$, $L^{ir} > 0$ denote arbitrary scalars, representing the bias generated by the non-pulsatile signal components:

$$R_1(L^{red}, L^{ir}) = \frac{\log\left(\frac{I_H^{red} - L^{red}}{I_L^{red} - L^{red}}\right)}{\log\left(\frac{I_H^{ir} - L^{ir}}{I_L^{ir} - L^{ir}}\right)}$$

It can be shown that $R_1(I_0 K_1^{red}, I_0 K_1^{ir}) = R$. The desired constants $L^{red} = I_0 K_1^{red}$ can be found during a calibration process, where a gold standard measurement provides the true R value $R = R_{true}$ and the resulting constants $(L^{red}, L^{ir})$ are optimized to fulfill the equation $R_1(L^{red}, L^{ir}) = R_{true}$.

Examples

Figure 8:
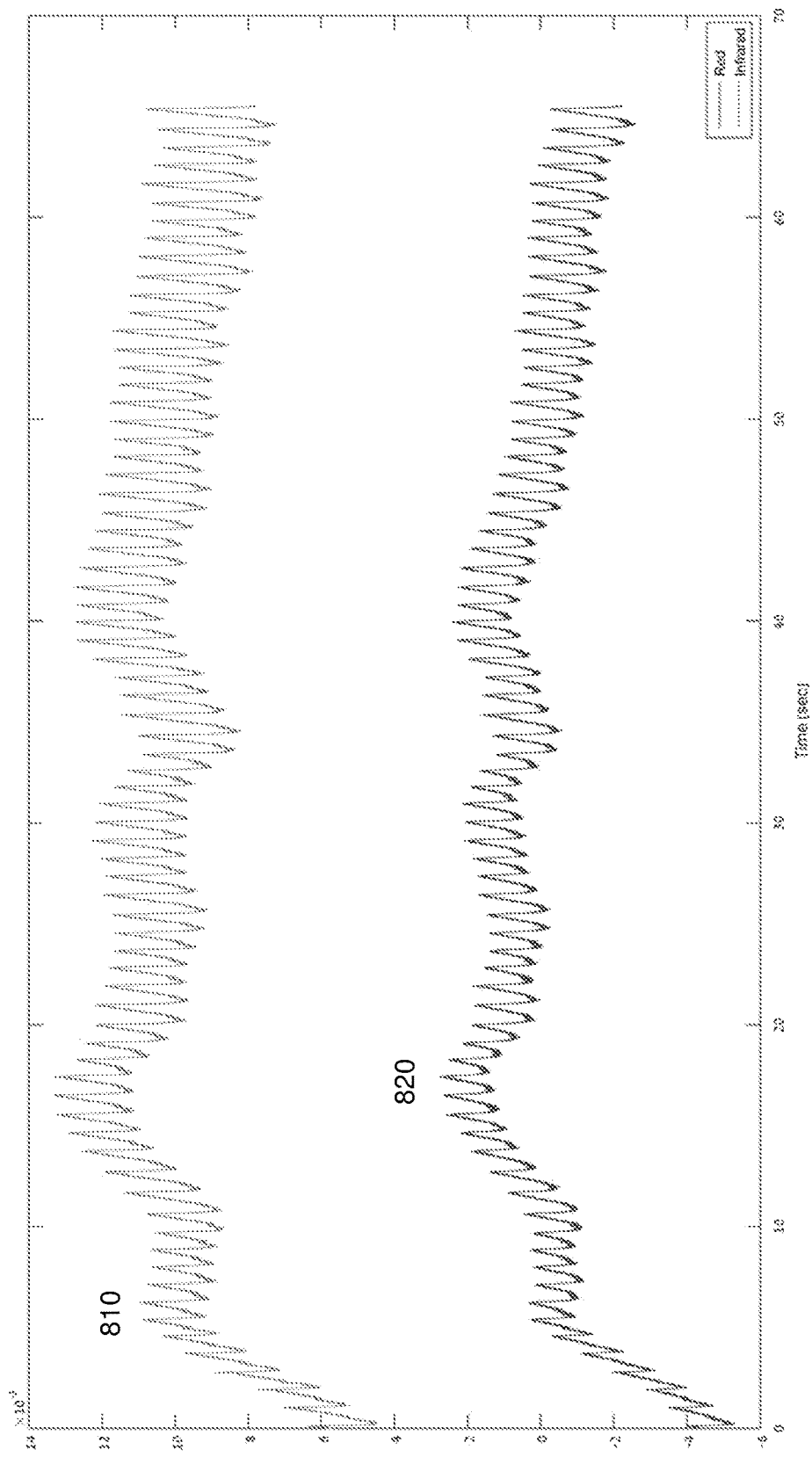
FIG. 8 illustrates example plots of a raw infrared PPG signal and a raw red PPG signal.

FIG. 8 illustrates example plots of a raw infrared signal 810 and raw red signal 820 measured during a period of 1 minute. The red signal 820 can be shifted.

Figure 9:
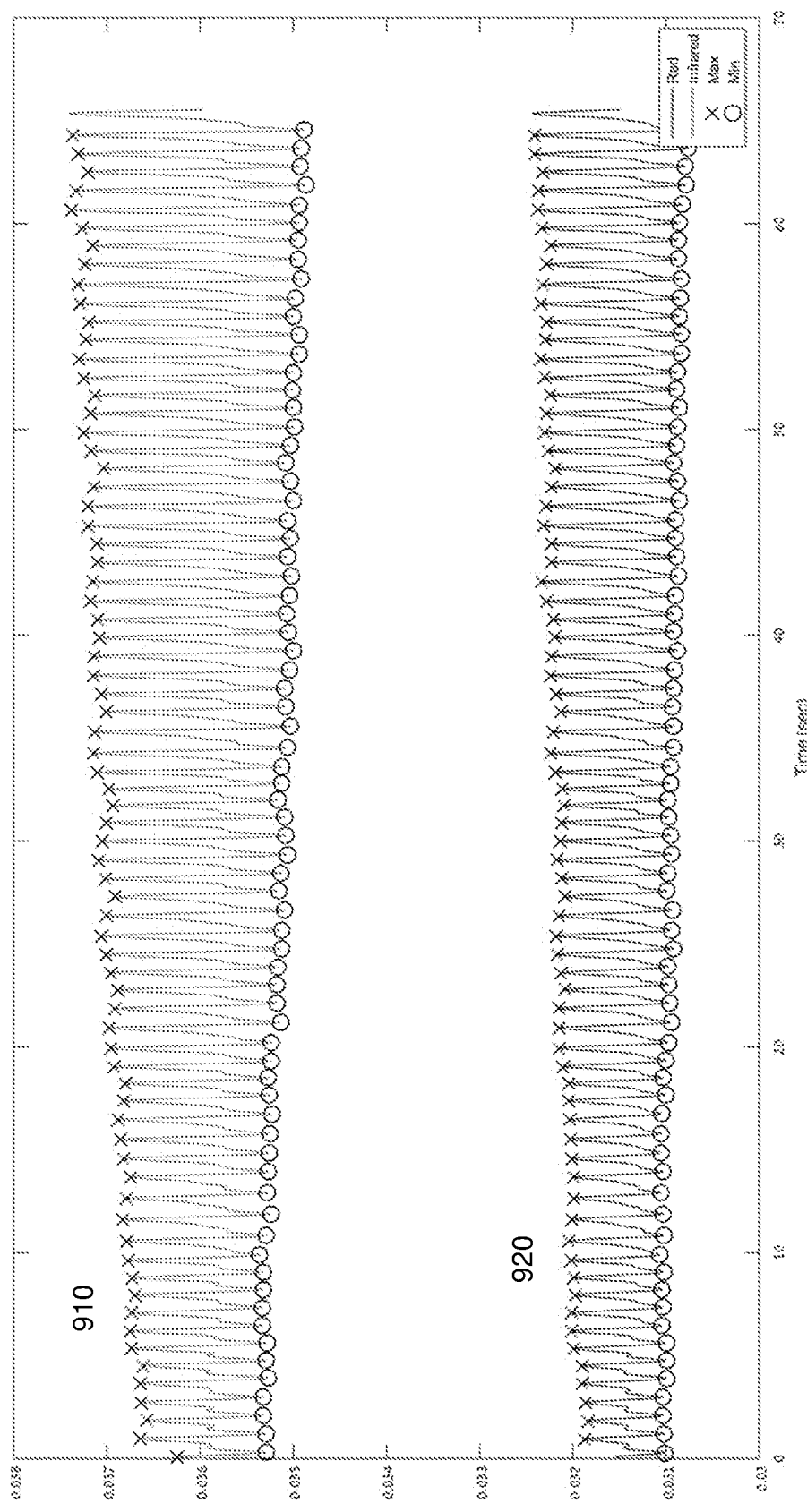
FIG. 9 illustrates example plots of a band-pass filtered infrared PPG signal and a band-passed filtered red PPG signal.

FIG. 9 illustrates example plots of infrared signal 910 and red signal 920. The infrared signal 810 can be obtained from the raw infrared signal 810 by band-pass filtering. The red signal 920 is band-passed filtered raw red signal 820.

Figure 10:
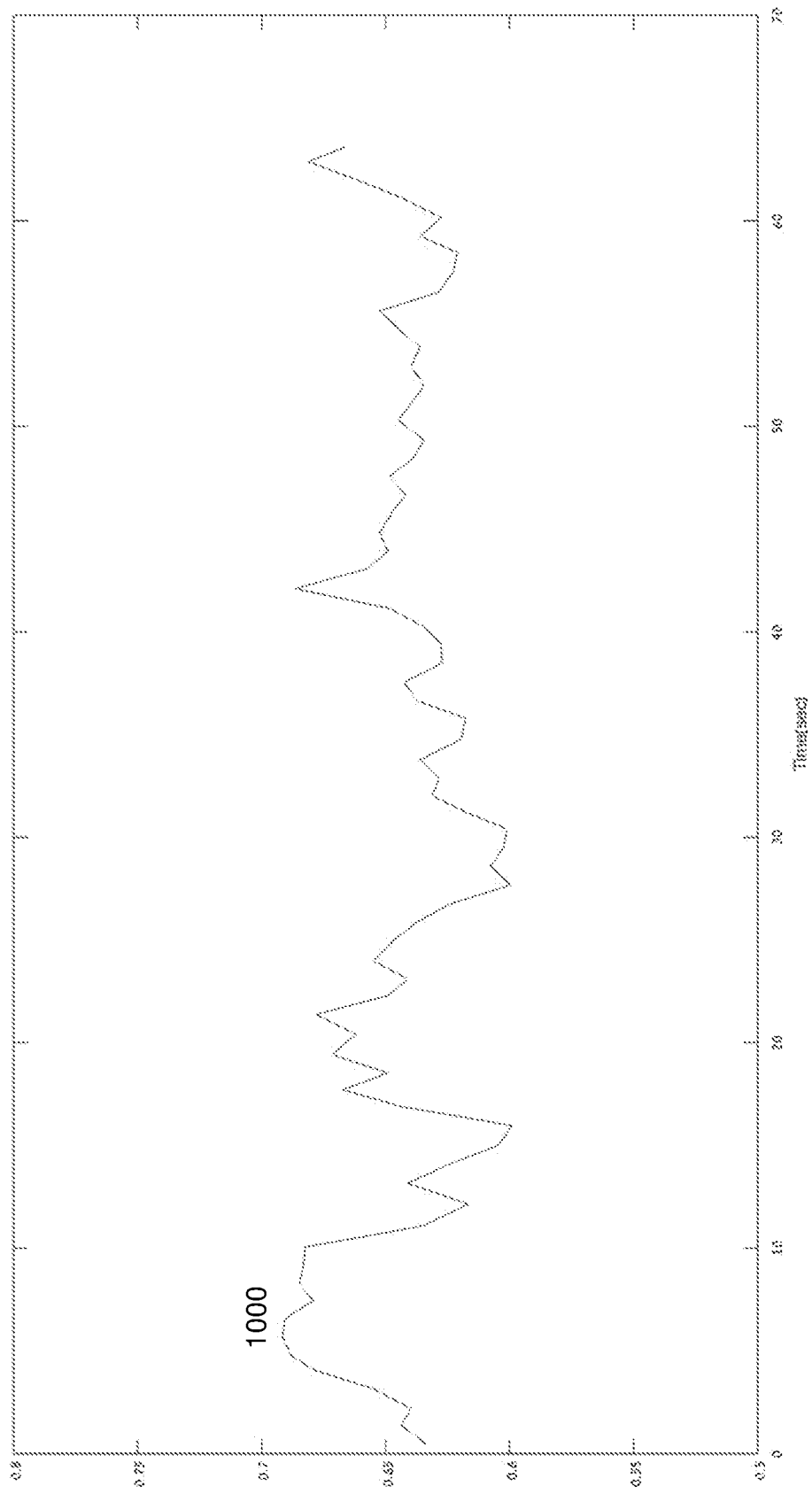
FIG. 10 illustrates an example plot of a ratio for determining the $SpO_2$ oxygen saturation.

FIG. 10 illustrates an example plot of a ratio 1000 for determining the SpO$_2$ saturation. The ratio 1000 can be determined based on the band-filtered infrared signal 910 and red signal 920 using the method of embodiment No 1 described above.

The present technology is described above with reference to example embodiments. Therefore, other variations upon the example embodiments are intended to be covered by the present disclosure.

What is claimed is:

1. A system for monitoring health status of a patient, the system comprising:
    a wearable device including at least one electrical sensor and at least one optical sensor, wherein:
        the at least one electrical sensor includes at least two electrodes configured to touch a surface of skin of a wrist of the patient covered by the wearable device, the at least one electrical sensor being configured to record, via the at least two electrodes, electrocardiogram (ECG) data from the surface of skin; and
        the at least one optical sensor includes an array of light sensors, wherein the light sensors are arranged in staggered rows to ensure that at least one light sensor from the array is positioned substantially near a pulsating blood artery of the wrist when the wearable device is disposed on the wrist, the at least one optical sensor being configured to record, via the at least one light sensor, photoplethysmogram (PPG) data from human tissue, the human tissue including the pulsating blood artery and a non-pulsatile tissue including the surface of a skin covering the pulsating blood artery and near-surface tissues underlying the skin and covering the pulsating blood artery, and wherein the wearable device is configured to apply a pre-determined amount of pressure to the wrist each time the patient wears the wearable device to provide for the same conditions for a reflection of a light from the surface of skin; and
    a processor communicatively coupled to the at least one electrical sensor and the at least one optical sensor, the processor being configured to:
        analyze the ECG data and the PPG data to obtain medical parameters associated with at least one chronic disease, wherein the analysis includes obtaining a modified PPG signal by removing, from the PPG data, an additive contribution resulting from the reflection of the light from the surface of the skin covering the pulsating blood artery and the near-surface tissues underlying the skin and covering the pulsating blood artery and keeping, in the PPG data, a contribution resulting from the reflection of the light from the pulsating blood artery unchanged, wherein the additive contribution is predetermined using a calibration process and at least one of the medical parameters is determined based on a ratio of an alternating current (AC) component and a direct current (DC) component of the modified PPG signal;
        detect changes in the medical parameters over time; and
        determine, based at least partially on the changes in the medical parameters, a progression or a remission of the at least one chronic disease, the changes being indicative of worsening or improving of the at least one chronic disease.

2. The system of claim 1, wherein the wearable device further includes at least one motion sensor.

3. The system of claim 1, wherein the wearable device includes a wristband operable to be placed around the wrist of the patient, the wristband including a sensor area, the sensor area including the at least one electrical sensor and the at least one optical sensor, the sensor area being arranged to cover at least a radial artery of the patient.

4. The system of claim 1, wherein the medical parameters include at least one of the following: an oxygen saturation, a tissue oxygen saturation, a cardiac output, a vascular resistance, a pulse rate, a blood pressure, a respiration, and motion data.

5. The system of claim 1, wherein the at least one chronic disease includes at least one of the following: a congestive heart failure, a hypertension, an arrhythmia, an asthma, a chronic obstructive pulmonary disease, a hypoglycemia, a sleep apnea, and a Parkinson's disease.

6. The system of claim 1, wherein the determination of the progression includes estimation of a deviation of at least one of the medical parameters from expected medical parameters, the expected medical parameters being based on individual historical medical parameters of the patient.

7. The system of claim 6, wherein if the deviation of the at least one of the medical parameters is larger than a pre-determined deviation value, the wearable device is further configured to:
    alert at least one of the following: the patient, a doctor, a relative of the patient, and a caretaker of the patient; and
    advise the patient to contact a medical professional.

8. The system of claim 6, wherein if the deviation of the at least one of the medical parameters is larger than a pre-determined value, the wearable device is further configured to provide an alert message to the patient, the alert message including an advisory to take medicine.

9. The system of claim 6, wherein when the deviation of the medical parameters is less than a pre-determined value, the processor is configured to repeatedly message the patient to assure the patient of a normal health status.

10. The system of claim 6, wherein when the deviation of the medical parameters is less than a pre-determined value, the wearable device is configured to repeatedly provide a sound signal to the patient to assure that the patient of a normal health status.

11. The system of claim 1, wherein the wearable device is communicatively coupled to a mobile device, the mobile device being configured to:
receive the medical parameters from the wearable device; and
process the medical parameters to provide to the patient at least one report regarding the health status of the patient.

12. The system of claim 11, wherein the mobile device is communicatively coupled to a cloud-based computing resource, the cloud-based computing resource being configured to:
receive the medical parameters from the mobile device for further analysis; and
provide at least one application for generating, based on the medical parameters, at least one report regarding the health status of the patient.

13. A method for monitoring health status of a patient, the method comprising:
providing at least one electrical sensor integrated into a wearable device, the at least one electrical sensor including at least two electrodes configured to touch a surface of skin of a wrist of the patient, the wearable device covering the surface of the skin, the at least one electrical sensor being configured to record, via the at least two electrodes, electrocardiogram (ECG) data from the surface of skin;
providing at least one optical sensor integrated into the wearable device, the at least one optical sensor including an array of light sensors, wherein the light sensors are arranged in staggered rows to ensure that at least one light sensor from the array is positioned substantially near a pulsating blood artery of the wrist when the wearable device is disposed on the wrist, the at least one optical sensor being configured to touch the surface of skin and record, via the at least one light sensor, photoplethysmogram (PPG) data from human tissue, the human tissue including the pulsating blood artery and a non-pulsatile tissue including the surface of a skin covering the pulsating blood artery and near-surface tissues underlying the skin and covering the pulsating blood artery, and wherein the wearable device is configured to apply a pre-determined amount of pressure to the wrist each time the patient wears the wearable device to provide for the same conditions for a reflection of a light from the surface of skin;
analyzing, by a processor communicatively coupled to the at least one electrical sensor and the at least one optical sensor, the ECG data and the PPG data to obtain medical parameters associated with at least one chronic disease, wherein the analysis includes obtaining a modified PPG signal by removing, from the PPG data, an additive contribution resulting from the reflection of the light from the surface of the skin covering the pulsating blood artery and the near-surface tissues underlying the skin and covering the pulsating blood artery and keeping, in the PPG data, a contribution resulting from the reflection of the light from the pulsating blood artery unchanged, and wherein the additive contribution is predetermined using a calibration process and at least one of the medical parameters is determined based on a ratio of an alternating current (AC) component and a direct current (DC) component of the modified PPG signal;
detecting, by the processor, changes in the medical parameters over time; and
determining, by the processor based at least partially on the changes in the medical parameters, a progression or a remission of the at least one chronic disease, the changes being indicative of worsening or improving of the at least one chronic disease.

14. The method of claim 13, wherein: the at least one electrical sensor and the at least one optical sensor are placed within a sensor area of the wearable device, the wearable device being placed around the wrist of the patient, and the sensor area being arranged to cover at least a radial artery of the patient.

15. The method of claim 13, wherein:
the medical parameters include at least one of the following: an $SpO_2$ oxygen saturation, a tissue oxygen saturation, a cardiac output, a vascular resistance, a pulse rate, a blood pressure, a respiratory rate, and motion data; and
the at least one chronic disease includes at least one of the following: a congestive heart failure; a hypertension, an arrhythmia, an asthma, a chronic obstructive pulmonary disease, a hypoglycemia, a sleep apnea, and a Parkinson's disease.

16. The method of claim 13, wherein determining the progression includes estimation of deviation of the at least one of the medical parameters from normal medical parameters, the normal medical parameters derived based on previously collected individual medical parameters of the patient.

17. The method of claim 16, further comprising: if the deviation of at least one of the medical parameters is larger than a pre-determined value:
providing an alert message to at least one of the following: the patient, a doctor, a relative of the patient, and a caretaker of the patient; and
providing at least one of the following:
advice to the patient to contact a medical professional; and
an alert message to the patient advising the patient to take medicine.

18. The method of claim of claim 16, further comprising, when the deviation of the at least one of the medical parameters is less than a pre-determined deviation value, providing repeatedly at least one of the following to the patient to assure the patient of a normal health status: a message and a sound signal.

19. A non-transitory computer-readable storage medium having embodied thereon a program, the program being executable by a processor to perform steps of a method for monitoring health status of a patient, the method comprising:
providing at least one electrical sensor integrated into a wearable device, the at least one electrical sensor including at least two electrodes configured to touch a surface of skin of a wrist of the patient covered by the wearable device, the at least one electrical sensor being configured to record, via the at least two electrodes, electrocardiogram (ECG) data from the surface of skin;

providing at least one optical sensor integrated into the wearable device, the at least one optical sensor including an array of light sensors, wherein the light sensors are arranged in staggered rows to ensure that at least one light sensor from the array is positioned substantially near a pulsating blood artery of the wrist when the wearable device is disposed on the wrist, the at least one optical sensor being configured to touch the surface of skin and record, via the at least one light sensor, photoplethysmogram (PPG) data from human tissue, the human tissue including the pulsating blood artery and a non-pulsatile tissue including the surface of a skin covering the pulsating blood artery and near-surface tissues underlying the skin and covering the pulsating blood artery, and wherein the wearable device is configured to apply a pre-determined amount of pressure to the wrist each time the patient wears the wearable device to provide for the same conditions for a reflection of a light from the surface of skin;

analyzing, by a processor communicatively coupled to the at least one electrical sensor and the at least one optical sensor, the ECG data and the PPG data to obtain medical parameters associated with at least one chronic disease, wherein the analysis includes obtaining a modified PPG signal by removing, from the PPG data, an additive contribution resulting from the reflection of the light from the surface of the skin covering the pulsating blood artery and the near-surface tissues underlying the skin and covering the pulsating blood artery and keeping, in the PPG data, a contribution resulting from the reflection of the light from the pulsating blood artery unchanged, and wherein the additive contribution is predetermined using a calibration process and at least one of the medical parameters is determined based on a ratio of an alternating current (AC) component and a direct current (DC) component of the modified PPG signal;

detecting, by the processor, changes in the medical parameters over time; and determining, by the processor based at least partially on the changes in the medical parameters, a progression or a remission of the at least one chronic disease, the changes being indicative of worsening or improving of the at least one chronic disease.

20. The system of claim 1, wherein the processor is further configured to:

analyze at least the PPG data to obtain a sinus arrhythmia waveform; and determine, based on the sinus arrhythmia waveform, a respiratory rate.

* * * * *